United States Patent
Saathoff

(10) Patent No.: US 6,610,081 B2
(45) Date of Patent: Aug. 26, 2003

(54) METHODS FOR TREATING MIGRAINE HEADACHES

(76) Inventor: Myra K. Saathoff, 3010 Oak Forest, Houston, TX (US) 77018

( * ) Notice: Subject to any disclaimer, the term of this patent is extended or adjusted under 35 U.S.C. 154(b) by 0 days.

(21) Appl. No.: 09/837,607

(22) Filed: Apr. 18, 2001

(65) Prior Publication Data

US 2002/0156508 A1 Oct. 24, 2002

(51) Int. Cl.⁷ .............................. A61N 1/05; G02C 9/00
(52) U.S. Cl. ........................... 607/88; 351/47; 351/163; 351/177
(58) Field of Search .............................. 607/88; 351/44, 351/47, 163, 166, 177

(56) References Cited

U.S. PATENT DOCUMENTS

| | | | | | |
|---|---|---|---|---|---|
| 4,940,323 | A | * | 7/1990 | Downing | 351/203 |
| 5,598,230 | A | * | 1/1997 | Queresima | 351/44 |
| 5,715,030 | A | * | 2/1998 | Quaresima | 351/44 |
| 6,105,925 | A | * | 8/2000 | Lossman et al. | 249/117 |
| 6,386,701 | B1 | * | 5/2002 | Khulusi | 351/45 |

* cited by examiner

*Primary Examiner*—Pamela Wilson
(74) *Attorney, Agent, or Firm*—The Matthews Firm

(57) ABSTRACT

The present invention generally relates to various systems and methods for the treatment of a migraine headache and related malady(s) through the filtering a portion of ambient light transmitted to the eye of a patient.

48 Claims, 1 Drawing Sheet

METHODS FOR TREATING MIGRAINE HEADACHES

FIELD OF THE INVENTION

The present invention generally relates to methods and apparatuses for treating migraine headaches and related maladies. An embodiment of the method generally comprises the filtering of a portion of ambient light transmitted into the eye of a patient.

BACKGROUND OF THE INVENTION

Migraine headaches are a very common disorder that afflicts numerous people on a regular basis. A migraine headache has been defined in the art, generally, as an episodic headache lasting a finite time, in the range of a small amount of time to days. The small amount of time could be minutes to a few hours. These episodic headaches are often, but not always, associated with an aura followed by gastrointestinal discomfort, dizziness, pulsatile pain, increased pain through normal physical activity, photophobia, phonophobia and/or visual disturbances. It is common that the discomfort and disturbance is of such a nature and frequencies so as to adversely affect the afflicted individual's lifestyle.

As used herein, the following terms mean and refer to the definitions given. The term "patient" means and refers to an individual afflicted with a migraine headache. The term "migraine headache" means and refers to an episodic headaches are often, but not always, associated with gastrointestinal discomfort, dizziness, pulsatile pain, increased pain through normal physical activity, photophobia, phonophobia and/or visual disturbances. The term "maladies" or "malady" means and refers to premenstrual syndrome, stress, and other related types of maladies, including migraine headaches. The term "filter" or "filtering" means and refers to filtering, interfering, shading, at least partially blocking and the like.

In response to such suffering the art field has developed numerous treatments that have proven effective if applied at the appropriate time. These treatments range from drugs to the application of various devices. However, none of the prior art methods for treating migraine headaches have taught or disclosed the treatment of a migraine headache through the filtering of a portion of a portion of light transmitted to the eye of a patient without the use of an auxiliary light source.

Numerous prior art methods treat migraine headaches through the administration of a drug or combination of drugs. Such prior art methods can be found in U.S. Pat. No. 5,914,129 to Mauskop, U.S. Pat. No. 5,538,959 to Mauskop, U.S. Pat. No. 4,024,279 to Zoc et al, U.S. Pat. No. 4,786,643 to Sanger et al., U.S. Pat. No. 4,916,125 to Herrling et al., U.S. Pat. No. 5,273,759 to Simmons, U.S. Pat. No. 5,639,784 to Hammarberg et al., U.S. Pat. No. 5,693,638 to Myers, U.S. Pat. No. 6,077,539 to Plachetka et al., U.S. Pat. No. 5,855,884 to Theoharides, U.S. Pat. No. 5,981,526 to Hargreaves, U.S. Pat. No. 6,103,218 to Brucker et al., and others. These aforementioned patents involve the treatment of a migraine headache through the administration of a pharmaceutical compound to a patient. However, such treatments do involve the ingestion of various drugs that can have negative effects in some patients. Accordingly, the art field is in search of a method for treating migraine headaches without the ingestion of drugs through the modification of a light transmitted to the eye.

The art field has developed several methods for treating a migraine headache without the ingestion of drugs. Examples of such applications are found in U.S. Pat. No. 5,795,150 to Boyd (the '150 patent), U.S. Pat. No. 5,513,656 to Boyd, Sr. (the '656 patent), U.S. Pat. No. 4,856,526 to Liss et al. (the '526 patent), U.S. Pat. No. 4,509,521 to Barry (the '521 patent), and U.S. Pat. No. 5,419,758 to Vijayam (the '758 patent). While these patents are directed towards treatments and preventative measures for migraine headaches, the treatment methods are not very convenient nor readily available in all cases.

The '150 patent and the '656 patent treat migraine headaches by attempting to prevent its occurrence through the prevention of chronic tension. These patents prevent chronic tension by the patient wearing an intra-oral device. The device is worn by a patient about the maxillary incisors such that a patient may not clench their teeth. The device is designed to be worn by a patient at all times, but is removable for eating. However, such a device can prove an irritant because it must always be worn. Additionally, the device is only effective in preventing migraine headaches that are caused by chronic tension and may not be effective in preventing migraine headaches caused by other factors. Accordingly, the art field is in search of a method of treating a migraine headache that does not require the wearing of an intrusive and uncomfortable device and a method that has a greater effect on the treatment of various migraine headaches.

The '758 patent teaches and discloses the use of an elastic band worn about the head of a patient to compress dilated blood vessels in order to provide relief of migraine headache pain. Rubber disks may be inserted between the band and the scalp to provide a more localized pressure over areas with a more severe pain. However, the wearing of such a device may be both uncomfortable and inconvenient. Additionally, the constricting of blood flow in the areas about the head may be dangerous if used by a patient without medical supervision. Accordingly, the art field is in search of a method of treating a migraine headache that does not require the restriction of blood flow through a self-applied elastic band.

The '521 patent and the '526 patent disclose a migraine and headache relief apparatus that relieves through the application of electric pulses. However, the use of electric pulses to an area about the cranium of a patient may be dangerous unless performed under the supervision of a doctor and such treatment may be too evasive for some patients. Accordingly, the art filed is in search of a method of treating migraine headaches without the use of electric pulses about the cranium of a patient.

Other prior art methods of treating migraine headaches and related maladies have concentrated on the pulsating of a laser light to the afflicted areas. Such prior art examples are found in U.S. Pat. No. 5,514,168 to Friedman (the '168 patent) and U.S. Pat. No. 5,640,978 to Wong (the '978 patent). However, both of these patents may not be entirely effective and require the availability of a laser light system for use.

The '168 patent discloses and teaches the application of a low power laser light to an intra-oral zone of tenderness often encountered in migraine headaches. However, not all migraine headaches produce an intra-oral zone of tenderness. Therefore the art field is in search of a method of treating a migraine headache that can treat a wider variety of migraine headaches and not just those caused by tension. Further, the art field is in search of a method of treating a migraine headache that does not require application of a laser light.

The '978 patent is directed more broadly to the treatment of a variety of muscular pains. A probe is laced in proximity to a pain, such as a muscular pain from a migraine headache, and low pulses of a laser are transmitted to the muscle. However, this method requires the availability of a laser system and may be too evasive for some patients. Therefore, the art field is in search of a method of treating a migraine headache that does not require a laser.

The prior art has used various optical devices to treat color blindness and related maladies, but not to relieve a migraine headache. Examples of such devices and methods are U.S. Pat. No. 3,586,423 to Zeltzer (the '423 patent), U.S. Pat. No. 3,701,590 to Zeltzer (the '590 patent), U.S. Pat. No. 4,300,819 to Taylor (the '819 patent), U.S. Pat. No. 4,848,894 to Buser et al. (the '894 patent), U.S. Pat. No. 4,998,817 to Zeltzer (the '894 patent), U.S. Pat. No. 5,363,152 to Reed, III (the '152 patent), U.S. Pat. No. 5,408,278 to Christman (the '278 patent), U.S. Pat. No. 5,617,154 to Hoffman (the '154 patent), U.S. Pat. No. 5,774,202 to Abraham et al. (the '204 patent), U.S. Pat. No. 5,846,457 to Hoffman (the '457 patent), U.S. Pat. No. 6,089,712 to Harris (the '712 patent), and U.S. Pat. No. 6,132,044 to Sternbergh (the '044 patent). However, these patents do not teach or suggest the modification of a light source transmitted to an eye for the treatment of a migraine headache.

Some prior art patents have taught that pulsating light into the eye of a patient suffering from a migraine headache may offer relief. Examples of such patents are U.S. Pat. No. 5,092,669 to Anderson (the '669 patent). The '669 patent discloses the flashing of a light into the eyes of a patient wearing goggles designed to filter all light transmittance. The '669 patent teaches that it is necessary to filter all ambient light entering the eye of a patient. Preferred embodiments of the '669 patent flash alternating lights into closed eyes of a patient in the range of 0.5 to 50 Hz with a brightness, or intensity, not to exceed 2000 millicandela. The goggles of the '669 patent resemble swimmers goggles, but are different in that the plates over each eye are opaque with a an LED (light emitting diode) on each plate. The LED's are powered by electrical signals carried in wires from a control box. Flashes of light are then sent to the a patient wearing the goggles for between 5 to 60 minutes. However, the '669 patent does not teach or suggest the modification of a light source to the eye of a patient without filtering the transmittance of ambient light to the eye of a patient. Further, the '669 patent does not tech or suggest the filtering of a portion of ambient light transmittance to the eye of a patient suffering from a migraine headache for relief of the migraine headache.

SUMMARY

The present invention generally relates to the treatment of a patient suffering from a migraine headache and related maladies. The treatment generally comprises the filtering of a portion of ambient light transmittance to the eye of a patient for relief of symptoms.

This summary is not intended to be a limitation with respect to the features of the invention as claimed, and this and other objects can be more readily observed and understood in the detailed description of the preferred embodiment and the claims.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

GENERAL DESCRIPTION AND EMBODIMENTS OF MODES FOR CARRYING OUT THE INVENTION

Figure 1:
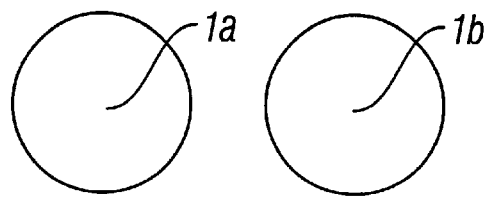
FIG. 1 is an illustration of an embodiment of the present invention.

Now referring to FIG. 1, an illustration of an embodiment of the present invention, a pair of lenses is disclosed. Lens 1a and lens 1b are designed as lenses to be worn over a portion of at least one eye of a patient. In an embodiment lenses 1a and 1b may be contact lenses. In another embodiment, only one lens is provided. Lenses 1a and 1b may constructed of any material common in the art and may include both hard lenses and soft lenses, as such term is well known in the art.

Lenses 1a and 1b may be fitted to the eye of a patient to cover a portion of at least one eye. In an embodiment, at least one of lenses 1a and 1b cover at least a portion of a cornea of at least one eye of a patient. In another embodiment, at least one of lenses 1a and 1b cover a portion less than the entire cornea of at least one eye of a patient. In another embodiment, at least a portion of lens 1a and/or 1b at least partially covers a portion of a cornea of at least one eye.

Lenses 1a and 1b are generally constructed of a material that partially filters or prevents the transmittance of a portion of the ambient light. In an embodiment, lenses 1a and 1b filter between about 30% to about 95% percent of ambient light from at least one eye of a patient. In another embodiment, lenses 1a and 1b filter between about 50% to about 80% percent of ambient light from the eyes of a patient. In yet another embodiment, lenses 1a and 1b filter between about 60% to about 75% percent of ambient light from at least one eye of a patient. However, various other embodiments may only filter a portion of ambient light transmittance to at least one eye of a patient. Further, other embodiments may filter varying portions of ambient light transmittance to the eyes of a patient through lens 1a and lens 1b, such that in a first eye a first portion is filtered through lens 1a and in a second eye a second portion is filtered through lens 1b.

The filtering of a portion of the ambient light from at least one eye of a patient may be accomplished by constructing the lenses 1a and 1b of a partially opaque material or tinting the lenses 1a and 1b. In an embodiment, lenses 1a and 1b may be constructed of a material that is partially translucent. In another embodiment, at least one of lenses 1a and 1b is constructed of a material that intermittently partially transparent, such that a portion of lens 1a and/or lens 1b is of varying translucency and/or transparency. Other embodiments may tint at least one of lenses 1a and 1b to a desired color. In an embodiment, at least one of lenses 1a and 1b is tinted.

The tinting of the lenses 1a and 1b may be of any color. In an embodiment, at least one of lenses 1a and 1b are tinted red. In another embodiment, the tinting is a rust red. In another embodiment, the tinting is a blue. In another embodiment, the tinting is a green. In another embodiment, the tinting is a color created by the mixing of red, green and blue. However, various embodiments of the present invention may use a tinting of any color.

A lens of the present invention may also be characterized by a wavelength of light that at least one lens allows to pass to at least one eye of a patient. In an embodiment, a lens of the present invention allows between about a wavelength of 590 nanometers (nm) to about a wavelength of 650 nm to pass to at least one eye of a patient. In another embodiment, a lens of the present invention allows between about a wavelength of 600 nm to about a wavelength of 635 nm to pass to at least one eye of a patient. In another embodiment, a lens of the present invention allows between about a wavelength of 615 nm to about a wavelength of 625 nm to pass to at least one eye of a patient. In another embodiment, a lens of the present invention about a wavelength of 620 nm to pass to at least one eye of a patient. However, varying other wavelengths of passage of light to at least one eye of a patient may be used with embodiments of the present invention.

Various embodiments of the present invention may utilize a lens 1a and 1b with a varying degree of density. In an embodiment, a density of lens 1a and/or lens 1b is between about 0.25 log units to about five (5) log units. In another embodiment, a density of lens 1a and/or 1b is between about 0.5 log units and about three (3) log units. In another embodiment, a density of a lens 1a and/or 1b is between about one (1) log unit to about two (2) log units. However, various embodiments of the present invention may utilize any density.

In various embodiments, lens 1a and lens 1b may be partially permeable. In an embodiment, lens 1a and/or lens 1b is permeable to oxygen. Other embodiments may be constructed of a material that is permeable to other gases, such as nitrogen, water vapor, and the like. However, various other embodiments may utilize lens 1a and/or lens 1b that are not permeable to gasses.

Figure 2:
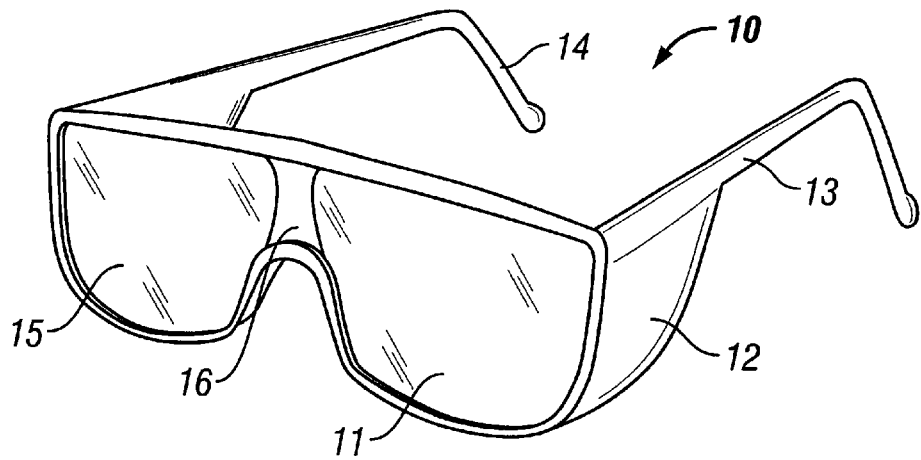
FIG. 2 is an illustration of an alternate embodiment of the present invention.

Now referring to FIG. 2, an illustration of an alternate embodiment of the present invention, a pair of goggles or eyeglasses 10 is disclosed. However, eyeglasses 10 may be a goggle, a mask, or any other suitable device common in the art for holding lenses to be worn over at least one eye of a patient.

Eyeglasses 10 are generally constructed of a first lens 11 and a second lens 15 in a frame 16. Frame 16 may have extension(s) 13 extending from frame 16 to ear piece(s) 14. A seal 12 is fitted about frame 16 to at least partially filter transmittance of light through first lens 11 and second lens 15.

Frame 16 may also have a portion for fitting about the nose of a patient. In an embodiment, frame 16 may have a portion for fitting over the nose of a patient. In another embodiment, frame 16 may have a portion that covers a portion of a nose of a patient.

First lens 11 and second lens 15 are generally constructed of a material that partially filters or prevents the transmittance of a portion of the ambient light past the lenses. In an embodiment, lenses 11 and 15 filter between about 30% to about 95% percent of ambient light from at least one eye of a patient. In another embodiment, lenses 11 and 15 filter between about 50% to about 80% percent of ambient light from at least one eye of a patient. In yet another embodiment, lenses 11 and 15 filter between about 60% to about 75% percent of ambient light from at least one eye of a patient. However, various other embodiments may only filter a portion of ambient light transmittance from at least one eye of a patient. Further, other embodiments may filter varying portions of ambient light transmittance to at least one eye of a patient through lens 11 and lens 15, such that in a first eye a first portion is filtered through lens 11 and in a second eye a second portion is filtered through lens 15. Other embodiments may filter differing portions of ambient light to at least one eye of a patient, such that.

The filtering of a portion of the ambient light from the eyes or eye of a patient may be accomplished by constructing the lenses 11 and 15 of a partially opaque material or tinting the lenses 11 and 15. In an embodiment, lenses 11 and 15 are constructed of a material that is partially translucent. In another embodiment, at least one of lenses 11 and 15 are constructed of a material that is partially translucent. Other embodiments may tint at least one of lenses 11 and 15 to a desired color. In an embodiment, at least one of lenses 11 and 15 are tinted.

The tinting of the lenses 11 and 15 may be of any color. In an embodiment, at least one of lenses 11 and 15 are tinted red. In another embodiment, the tinting is a rust red. In another embodiment, the tinting is a blue. In another embodiment, the tinting is a green. In another embodiment, the tinting is a color created by the mixing of red, green and blue. However, various embodiments of the present invention may use a tinting of any color.

A lens of the present invention may also be characterized by a wavelength of light that at least one lens allows to pass to at least one eye of a patient. In an embodiment, a lens of the present invention allows between about a wavelength of 590 nanometers (nm) to about a wavelength of 650 nm to pass to at least one eye of a patient. In another embodiment, a lens of the present invention allows between about a wavelength of 600 nm to about a wavelength of 635 nm to pass to at least one eye of a patient. In another embodiment, a lens of the present invention allows between about a wavelength of 615 nm to about a wavelength of 625 nm to pass to at least one eye of a patient. In another embodiment, a lens of the present invention about a wavelength of 620 nm to pass to at least one eye of a patient. However, varying other wavelengths of passage of light to at least one eye of a patient may be used with embodiments of the present invention.

In various embodiments, lens 11 and lens 15 may be partially permeable. In an embodiment, lens 11 and/or lens 15 is permeable to oxygen. Other embodiments may be constructed of a material that is permeable to other gases, such as nitrogen, water vapor, and the like. However, various other embodiments may utilize lens 11 and/or lens 15 that are not permeable to gasses.

Figure 3:
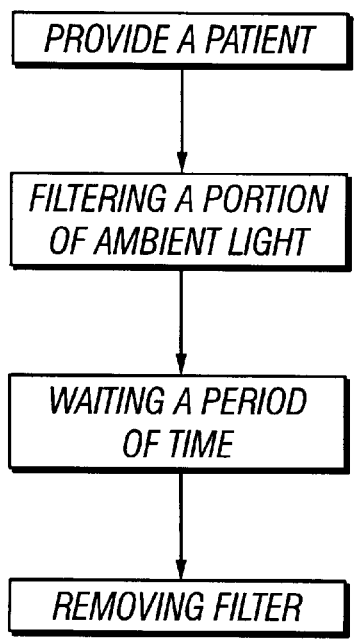
FIG. 3 is an illustration of an embodiment of a method of treatment of a patient.

The present invention further relates to a method of treatment of a patient suffering from symptoms of a migraine headache and related maladies. Now referring to FIG. 3, an illustration of an embodiment of a method of treatment of a patient, a general method of alleviation of migraine headaches and related maladies is disclosed. The method generally encompasses the treatment of a patient suffering from a migraine headache or related maladies by the filtering of a portion of ambient light transmitted to at least one eye of the patient.

In an embodiment, a patient is fitted with at least one lens which filters a portion of the ambient light transmitted to at least one eye of the patient. In another embodiment, the patient is fitted with a lens for each eye. Various embodiments utilize contact lenses, as herein described above, that are fitted to the eye(s) of the patient to cover at least a portion of the cornea. However, other embodiments of the present invention may utilize a pair of glasses, as herein described above, to filter a portion of the ambient light.

The lens(es) used for treatment of a patient can be constructed to filter a portion of the ambient light as herein described above. In an embodiment, the patient is fitted with a lens or lenses which filters between about 50% to about 95% percent of ambient light from the eye or eyes of a patient. In another embodiment, the lens or lenses filter between about 60% to about 80% percent of ambient light from the eyes of a patient. In yet another embodiment, the lens or lenses filter between about 65% to about 75% percent of ambient light from the eyes of a patient. However, various other embodiments may only filter a portion of ambient light transmittance to one eye of a patient. Further, other embodiments may filter varying portions of ambient light transmittance to the eyes of a patient through a first lens and a second portion through second lens. In this manner, a first portion of ambient light may be filtered to a first eye and a second portion of light may be filtered to a second eye. The portions of light filtered may vary depending on the treatment of the patient and the severity of the maladies.

In various embodiments of the method of treatment of a patient, the lens or lenses fitted to a patient may be tinted as herein described above. The tinting of the lens or lenses acts to specify the exact portion of light being transmitted to the eyes of a patient.

The portion of ambient light filtered from transmittance to the eye or eyes is continued from a period of time. In an embodiment, the portion of ambient light is filtered for between about 5 minutes to about 120 minutes. In another embodiment, the portion of light is filtered for between about 15 minutes to about 60 minutes. In yet another embodiment, the portion of ambient light is filtered for between about 25 minutes to about 45 minutes. However, the period of treatment through filtering a portion of the ambient light may vary according to the particular patient and severity of malady.

Other embodiments of the present invention may dim an ambient light source in an area about a patient. In an embodiment, the patient is in a room where the ambient light is dimmed, or lowered. The degree of dimming of the lights may vary from almost dark to only a slight dimming. However, other embodiments do not require that dimming of the ambient light.

Other embodiments of methods for relieving maladies further include the step of relaxing a patient. Such relaxation may be accomplished by removing external stimulus, quieting a room, speaking softly to the patient, asking the patient to relax, and the like. Results of the present invention have been shown to perform better, i.e., require less frequent treatments and/or medication, when the patient is relaxed. However, symptoms of maladies have been decreased and/or eliminated even when the patient fails to fully relax.

Results from the various methods herein described have shown to eliminate the symptoms from the maladies or substantially reduce discomfort from the maladies. The time of relief has been shown to be from days to months before a recurrence of the malady. Various treatments utilizing the method and apparatuses of the present invention have been shown to greatly reduce a frequency of occurrence of the malady.

The examples below illustrate embodiments of the present invention:

EXAMPLE 1

A patient was treated for symptoms of a migraine headache by placing a rust red tinted contact lens in each eye of the patient in a room where the ambient light was dimmed. The lenses were left in the eyes of the patient for about 30 minutes. When the lenses were removed no further symptoms of the migraine headache were felt. The symptoms did not return for the patient for a period of over six months.

EXAMPLE 2

A patient was treated for the symptoms of a migraine headache by placing a rust red contact lens was placed in each eye of the patient in a room where the light was not dimmed. The lenses were left in the eyes of the patient for about 120 minutes. When the lenses were removed, no further symptoms of the migraine were felt. The symptoms did not return for the patient for a period of over six months.

EXAMPLE 3

A patient was treated for a migraine headache. The patient was fitted with a pair of rust red tinted contact lenses for about forty-five (45) minutes in a room where the lights were dimmed. The patient has not experienced a relapse of the malady in over six (6) months.

EXAMPLE 4

A patient was treated for a PMS related migraine with a pair of rust red tinted contact lenses. The lenses were left in the eyes of the patient for a period of about 45 minutes in a dimly lit room. All symptoms of the malady were relieved. The patient uses a pair of the contact lenses about one or two days before her PMS cycle and is able to prevent any malady from returning.

EXAMPLE 5

A patient who had suffered from severe migraines for about fifty (50) years was fitted with a pair of contact lenses in a room where the ambient light was dimmed. The patient experienced relief from the symptoms of a migraine in about five (5) minutes. The patient did not relapse for over five (5) months.

What is claimed is:

1. A method of treating migraine headaches comprising the steps of:
    placing at least one contact lens on at least one eye of a patient whereby the lens filters a portion of an ambient light transmitted to the at least one eye;
    leaving the lens on the at least one eye for a period of time; and,
    removing the lens from the at least one eye whereby the migraine headache is relieved.
2. The method of claim 1 wherein the step of placing a contact lens on at least one eye of a patient further comprises placing a first contact lens on a first eye and placing a second contact lens on a second eye.
3. The method of claim 1 wherein the step of placing on at least one eye of a patient at least partially covers at least a portion of the eye of a patient.
4. The method of claim 1 wherein the step of placing on at least one eye of a patient at least partially covers at least a portion of the cornea of the eye of a patient.
5. The method of claim 1 wherein the step of placing on at least one eye of a patient at least partially covers the entire cornea of the eye of a patient.
6. The method of claim 1 wherein the step of placing on at least one eye of a patient at least partially covers at least a portion of the iris of the eye of a patient.
7. The method of claim 1 wherein the contact lens is tinted.
8. The method of claim 1 wherein the contact lens is at least partially opaque.

9. The method of claim 1 wherein the contact lens is tinted red.

10. The method of claim 1 wherein the contact lens is tinted rust red.

11. The method of claim 1 wherein the contact lens filters a portion of ambient light transmitted to the at least one eye of a patient.

12. The method of claim 1 wherein the contact lens filters between about 50% to about 95% of the ambient light transmitted to the at least one eye of a patient.

13. The method of claim 1 wherein the contact lens filters between about 60% to about 80% of the ambient light transmitted to the at least one eye of a patient.

14. The method of claim 1 wherein the contact lens filters between about 65% to about 75% of the ambient light transmitted to the at least one eye of a patient.

15. The method of claim 1 wherein the contact lens is gas permeable.

16. The method of claim 1 wherein the contact lens is permeable to oxygen gas.

17. The method of claim 1 wherein the contact lens is left in the at least one eye for between about 5 minutes to about 120 minutes.

18. The method of claim 1 wherein the lens is left in the at least one eye for between about 15 minutes to about 60 minutes.

19. The method of claim 1 wherein the contact lens is left in the at least one eye for between about 25 minutes to about 45 minutes.

20. The method of claim 1 further comprising dimming the ambient light.

21. The method of claim 20 Wherein the ambient light is dimmed before the contact lens is placed in the at least one eye.

22. The method of claim 1 wherein the at least one contact lens allows transmittance of a light source of a wavelength of between about 590 nanometers to about 650 nanometers.

23. The method of claim 1 wherein the at least one contact lens allows transmittance of a light source of a wavelength of between about 600 nanometers to about 635 nanometers.

24. The method of claim 1 wherein the at least one contact lens allows transmittance of a light source of a wavelength of between about 615 nanometers to about 625 nanometers.

25. The method of claim 1 wherein the at least one contact lens allows transmittance of a light source of a wavelength of about 620 nanometers.

26. A system for the relief of a symptom of a migraine headache comprising at least one contact lens that filters a portion of an ambient light source to at least one eye of a patient wherein the at least one contact lens is placed over a portion of the ambient light source to the at least one eye of a patient.

27. The system of claim 26 wherein the contact lens filters between about 50% to about 95% of the ambient light.

28. The system of claim 26 wherein the contact lens filters between about 60% to about 80% of the ambient light.

29. The system of claim 26 wherein the contact lens filters between about 65% to about 75% of the ambient light.

30. The system of claim 26 wherein the contact lens is red.

31. The system of claim 26 wherein the contact lens is rust red.

32. The system of claim 26 wherein the contact lens is at least partially opaque.

33. The system of claim 26 wherein the contact lens placed in the at least one eye of a patient covers at least a portion of the cornea.

34. The system of claim 26 wherein the contact lens placed in the at least one eye of a patient covers at least a portion of the iris.

35. The system of claim 26 wherein the contact lens placed in the at least one eye of a patient allows transmittance of a light source of a wavelength of between about 590 nanometers to about 650 nanometers.

36. The system of claim 26 wherein the contact lens placed in the at least one eye of a patient allows transmittance of a light source of a wavelength of between about 600 nanometers to about 635 nanometers.

37. The system of claim 26 wherein the contact lens placed in the at least one eye of a patient allows transmittance of a light source of a wavelength of between about 615 nanometers to about 625 nanometers.

38. The method of claim 37 wherein the contact lens is tinted.

39. The method of claim 37 wherein the contact lens is tinted a rust red color.

40. The method of claim 37 wherein the contact lens covering at least one eye of a patient filters the ambient light and allows transmittance of a light with a wavelength of between about 600 nanometers to about 635 nanometers.

41. The method of claim 37 wherein the contact lens covering at least one eye of a patient filters the ambient light and allows transmittance of a light with a wavelength of between about 615 nanometers to about 625 nanometers.

42. The method of claim 37 wherein the contact lens covering at least one eye of a patient filters the ambient light and allows transmittance of a light with a wavelength of about 620 nanometers.

43. The method of claim 37 wherein the patient is relaxed by reducing outside stimulus.

44. The method of claim 37 wherein the period of time is between about five minutes to about 120 minutes.

45. The method of claim 37 wherein the period of time is between about fifteen minutes to about 60 minutes.

46. The method of claim 37 wherein the period of time is between about twenty-five minutes to about forty five minutes.

47. The system of claim 26 wherein the contact lens placed in the at least one eye of a patient allows transmittance of a light source of a wavelength of about 620 nanometers.

48. A method for treating a migraine headache comprising the steps of:

covering at least a portion of at least one eye of a patient with at least one contact lens whereby a portion of an ambient light source is filtered;

dimming the ambient light source about the patient;

relaxing a patient for a period of time; and, removing the at least one contact lens.

* * * * *